United States Patent [19]

Kohsaka et al.

[11] Patent Number: 5,355,719
[45] Date of Patent: Oct. 18, 1994

[54] DRAIN SEPARATOR IN GAS ANALYZER

[75] Inventors: Hiroji Kohsaka, Kusatsu; Tokihiro Tsukamoto, Kyoto, both of Japan

[73] Assignee: Horiba, Ltr., Kyoto, Japan

[21] Appl. No.: 911,325

[22] Filed: Jul. 10, 1992

[30] Foreign Application Priority Data

Aug. 17, 1991 [JP] Japan ................. 3-73030[U]

[51] Int. Cl.⁵ .................. G01N 1/34; B01D 5/00
[52] U.S. Cl. .................. 73/31.07; 73/863.21; 55/421; 210/248
[58] Field of Search ............ 73/31.07, 863.21, 867.81, 73/864.85, 863.43; 210/248; 55/421

[56] References Cited

U.S. PATENT DOCUMENTS

| | | | |
|---|---|---|---|
| 2,489,893 | 11/1949 | Johnson | 73/31.07 X |
| 2,703,015 | 3/1955 | Sykes | 73/863.21 |
| 2,876,860 | 3/1959 | Clark et al. | 55/421 X |
| 2,991,646 | 7/1961 | Wrightman et al. | 73/31.07 |
| 3,289,481 | 12/1966 | Barnes | 73/863.21 |
| 3,581,469 | 6/1971 | Davis et al. | 73/31.07 X |
| 3,933,449 | 1/1976 | Miselen | 55/422 X |
| 4,194,398 | 3/1980 | Gastrock | 73/863.21 X |
| 4,359,907 | 11/1982 | Morin, III et al. | 73/863.21 |
| 4,613,349 | 9/1986 | Drapp et al. | 73/200 X |
| 5,181,943 | 1/1993 | Weber | 55/345 |

FOREIGN PATENT DOCUMENTS

| | | | |
|---|---|---|---|
| 2526056 | 1/1976 | Fed. Rep. of Germany | B01D 45/12 |
| 381954 | 5/1973 | U.S.S.R. | 73/31.07 |
| 890125 | 12/1981 | U.S.S.R. | 73/863.21 |

OTHER PUBLICATIONS

"Simple monitoring of stack emissions"; *Electrical Review* vol. 203, No. 14, p. 41, Oct. 13, 1978.

*Primary Examiner*—Tom Noland
*Attorney, Agent, or Firm*—Poms, Smith, Lande & Rose

[57] ABSTRACT

A drain separator in a gas analyzer is provided to rapidly remove drain or condensate from a gas flow by creating a rotary motion in the gas flow prior to introducing it into a separating chamber. In an exemplary embodiment, separating chamber 2, formed as a downwardly divergent conical space, connects with gas-inlet passage 6 at its upper end and an exhaust gas-outlet passage 3 at the periphery of its base. A sample gas-outlet passage 8 is disposed within separating chamber 2 in a coaxially aligned, vertically spaced opposing relationship to gas-inlet passage 6. Rotation of the gas flow may be accomplished by a vane 7, disposed within gas-inlet passage 6. Upon introduction of the rotating gas flow into separating chamber 2, the pressure on the flow is reduced causing the drain to condense and become distributed about the circumference of the low pressure gas flow. A portion of the gas from the center of the low pressure gas flow containing little condensate then passes through sample gas-inlet passage 8 to a gas analyzer. At the same time the majority of the condensate and waste gas is removed from separating chamber 2 through exhaust gas-outlet passage 3.

7 Claims, 2 Drawing Sheets

DRAIN SEPARATOR IN GAS ANALYZER

BACKGROUND OF THE INVENTION

1. Field of the Invention

The present invention relates to a drain separator used in a sampling system of a gas analyzer.

2. Description of the Prior Art

It is very important to remove a drain or condensate contained in a sample gas in a gas analysis. A prior art drain separator for removing said condensate drain is shown in FIG. 2. Referring to FIG. 2, reference numeral 11 designates a funnel-shaped partition plate provided with a drain-outlet passage 12 connected therewith at a lower end thereof to form a separating chamber 13. Reference numeral 14 designates a sample gas-inlet passage spouting said sample gas along a circumferential wall 15. Reference numeral 16 designates a sample gas-outlet passage.

According to the above described construction, said condensate having a high density in the sample gas is stuck to said circumferential wall 15 of the separating chamber 13 by a centrifugal force generated when the sample gas revolves along the circumferential wall 15 of the separating chamber 13 to be separated. The treated sample gas, from which the condensate has been removed, is taken out into said sample gas-outlet passage 16.

However, a disadvantage of a drain separator having such construction, is that the sample gas is revolved in the separating chamber 13, so that the sample gas is temporarily retained in the separating chamber 13, decreasing the responsiveness of the gas analysis. Thus, it takes a time to take out the sample gas, from which the condensate has been separated, into the sample gas-outlet passage 16, whereby the sample gas is mixed with a gas, which is subsequently sent to a gas analyzer.

SUMMARY OF THE INVENTION

It is an object of the present invention to provide a drain separator capable of reducing the time required for taking out a sample gas into a sample gas-outlet passage and thus eliminating the above described disadvantage by a very simple improvement.

That is to say, a drain separator in a gas analyzer according to the present invention is characterized in that a sample gas-inlet passage revolving a sample gas to spout said sample gas into a separating chamber is connected with a side of a top portion of said separating chamber formed of a divergent conical space, with which a drain and exhaust gas-outlet passage is connected, and a gas-outlet of a sample gas-outlet passage is provided so as to face the gas-inlet.

According to the above described characteristic construction, not only is said sample gas spouted into the separating chamber having a wide space from said sample gas-inlet passage to be instantaneously placed under a pressure lower than that in the sample-inlet passage, whereby a drain easily condenses, but the spouted gas is also revolved, so that a gas containing the condensate having a high density is flung along a circumferential wall of the separating chamber, whereby the condensate adheres to said circumferential wall of the separating chamber.

On the other hand, in a central portion of said gaseous flow spouted into the separating chamber under the revolved condition the gas containing no drain or the gas of a lower density containing condensate in a very small quantity flows into said sample gas-outlet passage to be immediately removed as it is.

DETAILED DESCRIPTION OF THE PREFERRED EMBODIMENTS

Figure 1:
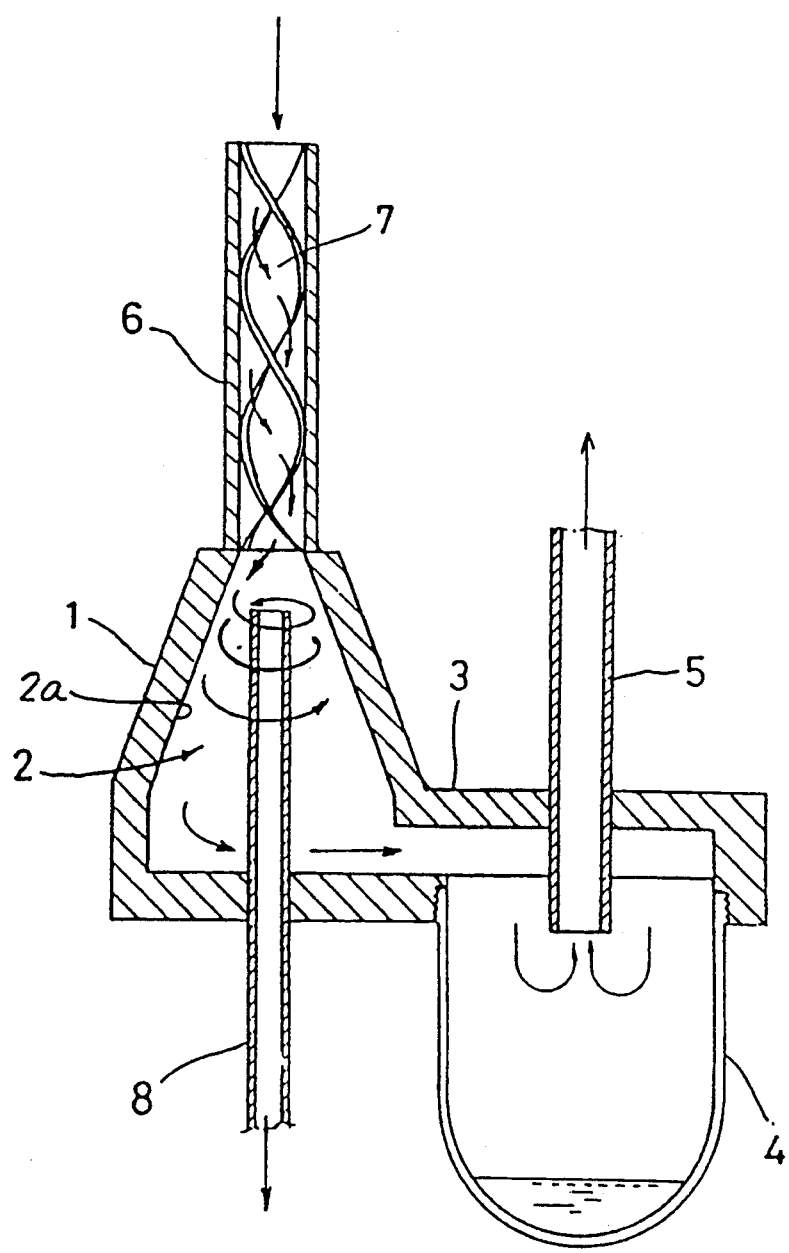
FIG. 1 is a sectional view showing a drain separator in accordance with the teachings of the present invention.
Figure 2:
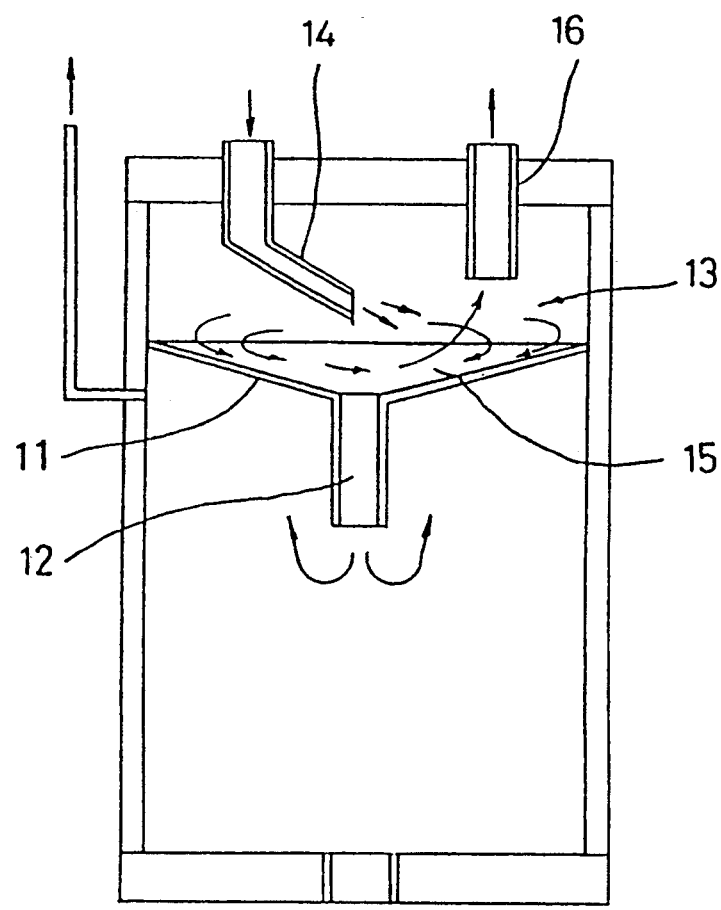
FIG. 2 is a sectional view showing a conventional drain separator.

The preferred embodiments of the present invention will be below described with reference to the drawings. FIG. 1 shows a drain separator according to one preferred embodiment of the present invention. Referring to FIG. 1, reference numeral 1 designates a case forming a separating chamber 2 formed of a divergent conical space and provided with a drain and exhaust gas-outlet passage 3 communicatively connected with a side of a lower portion thereof. Reference numeral 4 designates a drain pot and reference numeral 5 designates an exhaust gas pipe.

Reference numeral 6 designates a sample gas-inlet passage provided with a spiral member 7 having such a shape that a narrow paper tablet-like thin metallic plate is twisted therewithin and connected with a side of said separating chamber 2 coaxially with the separating chamber 2 so that a sample gas may be revolved to be spouted into the separating chamber 2.

Reference numeral 8 designates a sample gas-outlet passage having a diameter smaller (same as or slightly larger) than that of said sample gas-inlet passage 6 passing through a bottom plate portion of the separating chamber 2 and provided coaxially with the sample gas-inlet passage 6 so that sample gas-outlet passage 8 faces sample gas-inlet passage 6 at an appointed interval.

According to the above described construction, said sample gas is instantaneously placed under a pressure lower than that in the sample gas-inlet passage 6 when the sample gas is spouted into the separating chamber 2 having a wide space from the sample gas-inlet passage 6, so that a drain contained in the sample gas easily condenses, and the spouted gas is revolved, so that a gas containing said drain of a higher density or condensate is flung along a circumferential wall 2a of the separating chamber 2 so said condensate adheres to said circumferential wall 2a of the separating chamber 2, thereby separating the drain or condensate. The drain or condensate adhering to the circumferential wall 2a flows into said drain pot 4 through said drain and exhaust gas-outlet passage 3 together with an exhaust gas which is exhausted through said exhaust gas pipe 5.

On the other hand, in a central portion of the sample gas revolved to be spouted into the separating chamber 2, a gaseous flow containing no drain or condensate, or a gaseous flow containing the drain or condensate of a lower density in a very small quantity is immediately taken out into said sample gas-outlet passage 8 and is sent to a gas analyzer.

As above described, in the drain separator in a gas analyzer, according to the present invention, the sample gas is revolved to diffuse the gas containing the drain or condensate of a higher density within the separating chamber and remove the gas containing no condensate, or the gas containing the condensate in a very small quantity allowing said gas to flow through said central portion of the spiral instantaneously, as it is, so that the sample gas can be introduced into the gas analyzer, almost nullifying the time during which the gas remains within the separating chamber. Thus, highly responsive gas analysis can be speedily achieved.

What is claimed is:

1. A drain separator in a gas analyzer, characterized in that a sample gas-inlet passage revolving a sample gas to spout said sample gas into a separating chamber is connected with a side of a top portion of said separating chamber, formed of a divergent conical space, with which a drain and exhaust gas-outlet passage is connected, and a gas-outlet of a sample gas-outlet passage is provided so as to face to a gas-inlet.

2. A drain separator for a gas stream comprising:
   a vertically aligned downwardly diverging conical separating chamber having a gas inlet at its upper end and an exhaust gas outlet drain disposed at the periphery of its base;
   means for creating a circumferential rotary motion substantially perpendicular to the direction of flow of a gas stream directed through said inlet; and
   a gas outlet disposed within said separating chamber in coaxially aligned, vertically spaced, opposing relationship to said gas inlet.

3. The drain separator of claim 2 wherein said means for creating a rotary motion comprises:
   a vertically aligned inlet tube in fluid-conducting communication with said gas inlet; and
   a vane member disposed within said inlet tube.

4. The drain separator of claim 3 wherein said vane member is an annular helical flange coaxially disposed within said inlet tube.

5. The drain separator of claim 4 wherein said annular helical flange is a metallic double helix disposed within said inlet tube at a position adjacent to said gas inlet of said downwardly diverging conical separating chamber.

6. The drain separator of claim 2 wherein said gas outlet is smaller than said gas inlet.

7. The drain separator of claim 2 further comprising a vented drain pot in fluid conducting communication with said exhaust gas outlet drain.

* * * * *